US008449901B2

(12) United States Patent
Shanley et al.

(10) Patent No.: US 8,449,901 B2
(45) Date of Patent: May 28, 2013

(54) IMPLANTABLE MEDICAL DEVICE WITH BENEFICIAL AGENT CONCENTRATION GRADIENT

(75) Inventors: John F. Shanley, Redwood City, CA (US); Theodore L. Parker, Danville, CA (US); Kinam Park, West Lafayette, IN (US)

(73) Assignee: Innovational Holdings, LLC ( * ) Notice: Subject to any disclaimer, the term of this patent is extended or adjusted under 35 U.S.C. 154(b) by 1366 days.

(21) Appl. No.: 11/369,592

(22) Filed: Mar. 7, 2006

(65) Prior Publication Data
US 2006/0147489 A1 Jul. 6, 2006

Related U.S. Application Data

(60) Division of application No. 10/777,283, filed on Feb. 11, 2004, now abandoned, which is a continuation-in-part of application No. 10/402,893, filed on Mar. 28, 2003, now Pat. No. 7,056,338.

(51) Int. Cl.
*A61F 2/00* (2006.01)

(52) U.S. Cl.
USPC ........... 424/423; 424/422; 424/424; 424/425; 424/426

(58) Field of Classification Search
None
See application file for complete search history.

(56) References Cited

U.S. PATENT DOCUMENTS

| | | |
|---|---|---|
| 3,657,744 A | 4/1972 | Ersek |
| 4,300,244 A | 11/1981 | Bokros |
| 4,321,711 A | 3/1982 | Mano |
| 4,531,936 A | 7/1985 | Gordon |
| 4,542,025 A | 9/1985 | Tice et al. |
| 4,580,568 A | 4/1986 | Gianturco |
| 4,650,466 A | 3/1987 | Luther |
| 4,733,665 A | 3/1988 | Palmaz |
| 4,739,762 A | 4/1988 | Palmaz |
| 4,776,337 A | 10/1988 | Palmaz |
| 4,800,882 A | 1/1989 | Gianturco |
| 4,824,436 A | 4/1989 | Wolinsky |
| 4,834,755 A | 5/1989 | Silvestrini et al. |
| 4,955,878 A | 9/1990 | See et al. |
| 4,957,508 A | 9/1990 | Kaneko et al. |
| 4,960,790 A | 10/1990 | Stella et al. |
| 4,969,458 A | 11/1990 | Wiktor |
| 4,989,601 A | 2/1991 | Marchosky et al. |
| 4,990,155 A | 2/1991 | Wilkoff |
| 4,994,071 A | 2/1991 | MacGregor |
| 5,013,363 A | 5/1991 | Hakamatsuka et al. |
| 5,019,090 A | 5/1991 | Pinchuk |
| 5,049,132 A | 9/1991 | Shaffer et al. |
| 5,053,048 A | 10/1991 | Pinchuk |
| 5,059,166 A | 10/1991 | Fischell et al. |
| 5,059,211 A | 10/1991 | Stack et al. |
| 5,078,726 A | 1/1992 | Kreamer |
| 5,092,841 A | 3/1992 | Spears |
| 5,102,417 A | 4/1992 | Palmaz |
| 5,157,049 A | 10/1992 | Haugwitz et al. |
| 5,171,217 A | 12/1992 | March et al. |
| 5,171,262 A | 12/1992 | MacGregor |
| 5,176,617 A | 1/1993 | Fischell et al. |
| 5,195,984 A | 3/1993 | Schatz |
| 5,197,978 A | 3/1993 | Hess |
| 5,213,580 A | 5/1993 | Slepian et al. |
| 5,234,456 A | 8/1993 | Silvestrini |
| 5,242,399 A | 9/1993 | Lau et al. |
| 5,286,254 A | 2/1994 | Shapland et al. |
| 5,290,271 A | 3/1994 | Jernberg |
| 5,292,512 A | 3/1994 | Schaefer et al. |
| 5,304,121 A | 4/1994 | Sahatjian |
| 5,314,688 A | 5/1994 | Kauffman et al. |
| 5,342,348 A | 8/1994 | Kaplan |
| 5,342,621 A | 8/1994 | Eury |
| 5,344,426 A | 9/1994 | Lau et al. |
| 5,380,299 A | 1/1995 | Fearnot et al. |
| 5,383,892 A | 1/1995 | Cardon et al. |
| 5,383,928 A | 1/1995 | Scott et al. |
| 5,403,858 A | 4/1995 | Bastard et al. |
| 5,407,683 A | 4/1995 | Shively |

(Continued)

FOREIGN PATENT DOCUMENTS

| | | |
|---|---|---|
| CA | 2234787 | 10/1998 |
| DE | 20200220 | 4/2002 |

(Continued)

OTHER PUBLICATIONS

Hwang,C.W. et. al. "Physiological Transport Forces Govern Drug Distribution for Stent Based Delivery". Circulation, Aug. 17, 2001, pp. 1-8.
Emanelsson, H., et. al., The Jostent Coronary Stent Range, Chapter 19, 1997.
West, J.L., "Drug Delivery-Pulsed Polymers", Nature Materials, vol. 2, Nov. 2003 pp. 709-710.
Ran Kornowski, et al. (Washington Hospital, Wash. D.C.); "Slow-Release Taxol Coated GR11 Stents Reduce Neointima Formation in a Porcine Coronary in-Stent Rastenosis Model"; Abstract from the American Heart Association's 70th Scientific Sessions (Nov. 9-12, 1997).
David A. Cox, MD, et al.; "Effect of Local Delivery of Heparin and Methotrexate on Neointimal Proliferation in Stented Porcine Coronary Arteries"; Coronary Artery Disease, Mar. 1992, vol. 3, No. 3: 237-248; University of AL, USA.
Tom Lambert, et al.; "A New Method for Arterial Drug Delivery Via Removable Stent"; JACC vol. 21, No. 2, Feb. 1993, abstract 834-2; American College of Cardiology, Bethesda, MD, USA.
Dav: Circulation, 1993, 89 (2/2): 834-2.
Bonnie L. Hiatt, et al. "The Drug-Eluting Stent: Is It the Holy Grail?" Reviews in Cardiovascular Medicine. (2001) vol. 2, No. 4, pp. 190-196P032-C1.
Patrick W. Serruys, et al., "Heparin-Coated Palmaz-Schatz Stents in Human Coronary Arteries" Circulation, 1996; 93:412-422.

(Continued)

*Primary Examiner* — James W Rogers

(57) ABSTRACT

The implantable medical devices are configured to release at least one therapeutic agent from a matrix affixed to the implantable body with a release profile which is programmable to the agent and treatment. The matrix is formed such that the concentration of the therapeutic agent in the matrix varies as a gradient relative to a surface of the implantable body. The change in the concentration gradient of the agent in the matrix directly controls the rate of elution of the agent from the matrix. The therapeutic agent matrix can be disposed in the stent or on surfaces of the stent in various configurations, including within volumes defined by the stent, such as openings, holes, or concave surfaces, as a reservoir of agent, and alternatively as a coating on all or a portion of the surfaces of the stent structure.

11 Claims, 4 Drawing Sheets

U.S. PATENT DOCUMENTS

| | | |
|---|---|---|
| 5,415,869 A | 5/1995 | Straubinger et al. |
| 5,419,760 A | 5/1995 | Narciso |
| 5,439,446 A | 8/1995 | Barry |
| 5,439,686 A | 8/1995 | Desai et al. |
| 5,441,515 A | 8/1995 | Khosravi et al. |
| 5,441,745 A | 8/1995 | Presant et al. |
| 5,443,496 A | 8/1995 | Schwartz et al. |
| 5,443,497 A | 8/1995 | Venbrux |
| 5,443,500 A | 8/1995 | Sigwart |
| 5,447,724 A | 9/1995 | Helmus et al. |
| 5,449,373 A | 9/1995 | Pinchasik et al. |
| 5,449,513 A | 9/1995 | Yokoyama et al. |
| 5,457,113 A | 10/1995 | Cullinan et al. |
| 5,460,817 A | 10/1995 | Langley et al. |
| 5,462,866 A | 10/1995 | Wang |
| 5,464,450 A | 11/1995 | Buscemi et al. |
| 5,464,650 A | 11/1995 | Berg et al. |
| 5,472,985 A | 12/1995 | Grainger et al. |
| 5,473,055 A | 12/1995 | Mongelli et al. |
| 5,500,013 A | 3/1996 | Buscemi et al. |
| 5,512,055 A | 4/1996 | Domb et al. |
| 5,516,781 A | 5/1996 | Moris et al. |
| 5,523,092 A | 6/1996 | Hanson et al. |
| 5,525,357 A * | 6/1996 | Keefer et al. ............... 424/486 |
| 5,534,287 A | 7/1996 | Lukic |
| 5,545,208 A | 8/1996 | Wolff et al. |
| 5,545,210 A | 8/1996 | Hess et al. |
| 5,545,569 A | 8/1996 | Grainger et al. |
| 5,551,954 A | 9/1996 | Buscemi et al. |
| 5,554,147 A * | 9/1996 | Batich et al. ............... 604/890.1 |
| 5,556,413 A | 9/1996 | Lam |
| 5,563,146 A | 10/1996 | Morris et al. |
| 5,571,525 A | 11/1996 | Roorda et al. |
| 5,575,771 A | 11/1996 | Walinsky |
| 5,578,075 A | 11/1996 | Dayton |
| 5,593,434 A | 1/1997 | Williams |
| 5,595,722 A | 1/1997 | Grainger et al. |
| 5,599,844 A | 2/1997 | Grainger et al. |
| 5,605,696 A | 2/1997 | Eury et al. |
| 5,607,417 A * | 3/1997 | Batich et al. ............... 604/890.1 |
| 5,607,442 A | 3/1997 | Fischell et al. |
| 5,609,629 A | 3/1997 | Fearnot et al. |
| 5,616,608 A | 4/1997 | Kinsella et al. |
| 5,617,878 A | 4/1997 | Taheri |
| 5,618,299 A | 4/1997 | Khosravi et al. |
| 5,624,411 A * | 4/1997 | Tuch ............... 604/265 |
| 5,628,787 A | 5/1997 | Mayer |
| 5,637,113 A | 6/1997 | Tartaglia et al. |
| 5,643,314 A | 7/1997 | Carpenter et al. |
| 5,646,160 A | 7/1997 | Morris et al. |
| 5,660,873 A | 8/1997 | Nikolaychik et al. |
| 5,665,591 A | 9/1997 | Sonenshein et al. |
| 5,665,728 A | 9/1997 | Morris et al. |
| 5,667,764 A | 9/1997 | Kopia et al. |
| 5,674,241 A | 10/1997 | Bley et al. |
| 5,674,278 A | 10/1997 | Boneau |
| 5,679,400 A | 10/1997 | Tuch |
| 5,697,971 A | 12/1997 | Fischell et al. |
| 5,707,385 A | 1/1998 | Williams |
| 5,713,949 A | 2/1998 | Jayaraman |
| 5,716,981 A | 2/1998 | Hunter et al. |
| 5,725,548 A | 3/1998 | Jayaraman |
| 5,725,549 A | 3/1998 | Lam |
| 5,733,330 A | 3/1998 | Cox |
| 5,733,925 A | 3/1998 | Kunz et al. |
| 5,741,293 A | 4/1998 | Wijay |
| 5,759,192 A | 6/1998 | Saunders |
| 5,766,239 A | 6/1998 | Cox |
| 5,766,584 A | 6/1998 | Edelman et al. |
| 5,769,883 A | 6/1998 | Buscemi et al. |
| 5,770,609 A | 6/1998 | Grainger et al. |
| 5,773,479 A | 6/1998 | Grainger et al. |
| 5,776,181 A | 7/1998 | Lee et al. |
| 5,776,184 A | 7/1998 | Tuch |
| 5,780,807 A | 7/1998 | Saunders |
| 5,797,898 A | 8/1998 | Santini, Jr. et al. |
| 5,800,507 A | 9/1998 | Schwartz |
| 5,807,404 A | 9/1998 | Richter |
| 5,811,447 A | 9/1998 | Kunz et al. |
| 5,817,152 A | 10/1998 | Birdsall et al. |
| 5,824,045 A | 10/1998 | Alt |
| 5,824,049 A | 10/1998 | Ragheb et al. |
| 5,827,322 A | 10/1998 | Williams |
| 5,837,008 A | 11/1998 | Berg et al. |
| 5,837,313 A | 11/1998 | Ding et al. |
| 5,843,117 A | 12/1998 | Alt et al. |
| 5,843,120 A | 12/1998 | Israel et al. |
| 5,843,172 A | 12/1998 | Yan |
| 5,843,175 A | 12/1998 | Frantzen |
| 5,843,741 A | 12/1998 | Wong et al. |
| 5,853,419 A | 12/1998 | Imran |
| 5,855,600 A | 1/1999 | Alt |
| 5,868,781 A | 2/1999 | Killion |
| 5,873,904 A | 2/1999 | Ragheb et al. |
| 5,876,419 A | 3/1999 | Carpenter et al. |
| 5,882,335 A | 3/1999 | Leone et al. |
| 5,886,026 A | 3/1999 | Hunter et al. |
| 5,922,020 A | 7/1999 | Klein et al. |
| 5,922,021 A | 7/1999 | Jang |
| 5,928,916 A | 7/1999 | Keogh |
| 5,935,506 A | 8/1999 | Schmitz et al. |
| 5,945,456 A | 8/1999 | Grainger et al. |
| 5,957,971 A | 9/1999 | Schwartz |
| 5,964,798 A | 10/1999 | Imran |
| 5,968,092 A | 10/1999 | Buscemi et al. |
| 5,972,027 A | 10/1999 | Johnson |
| 5,972,180 A | 10/1999 | Chujo |
| 5,976,182 A | 11/1999 | Cox |
| 5,980,551 A | 11/1999 | Summers et al. |
| 5,980,972 A | 11/1999 | Ding |
| 5,981,568 A | 11/1999 | Kunz et al. |
| 5,984,957 A | 11/1999 | Laptewicz, Jr. et al. |
| 5,992,000 A | 11/1999 | Humphrey et al. |
| 5,992,769 A | 11/1999 | Wise et al. |
| 5,994,341 A | 11/1999 | Hunter et al. |
| 5,997,703 A | 12/1999 | Richter |
| 6,007,517 A | 12/1999 | Anderson |
| 6,017,363 A | 1/2000 | Hojeibane et al. |
| 6,019,789 A | 2/2000 | Dinh et al. |
| 6,022,371 A | 2/2000 | Killion |
| 6,030,414 A | 2/2000 | Taheri |
| 6,042,606 A | 3/2000 | Frantzen |
| 6,056,722 A | 5/2000 | Jayaraman |
| 6,063,101 A | 5/2000 | Jacobsen et al. |
| 6,071,305 A | 6/2000 | Brown et al. |
| 6,074,659 A | 6/2000 | Kunz et al. |
| 6,083,258 A | 7/2000 | Yadav |
| 6,087,479 A | 7/2000 | Stamler et al. |
| 6,096,070 A | 8/2000 | Ragheb et al. |
| 6,099,561 A | 8/2000 | Alt |
| 6,099,562 A | 8/2000 | Ding et al. |
| 6,120,535 A | 9/2000 | McDonald et al. |
| 6,120,536 A | 9/2000 | Ding et al. |
| 6,120,847 A | 9/2000 | Yang et al. |
| 6,121,027 A | 9/2000 | Clapper et al. |
| 6,123,861 A | 9/2000 | Santini, Jr. et al. |
| 6,131,266 A | 10/2000 | Saunders |
| 6,140,127 A | 10/2000 | Sprague |
| 6,153,252 A | 11/2000 | Hossainy et al. |
| 6,156,062 A | 12/2000 | McGuinness |
| 6,159,488 A | 12/2000 | Nagler et al. |
| 6,171,609 B1 | 1/2001 | Kunz |
| 6,174,326 B1 | 1/2001 | Kitaoka et al. |
| 6,193,746 B1 | 2/2001 | Strecker |
| 6,206,914 B1 | 3/2001 | Soykan et al. |
| 6,206,915 B1 | 3/2001 | Fagan et al. |
| 6,206,916 B1 | 3/2001 | Furst |
| 6,231,600 B1 | 5/2001 | Zhong |
| 6,239,118 B1 | 5/2001 | Schatz et al. |
| 6,240,616 B1 | 6/2001 | Yan |
| 6,241,762 B1 | 6/2001 | Shanley |
| 6,245,101 B1 | 6/2001 | Drasler et al. |
| 6,249,952 B1 | 6/2001 | Ding |
| 6,254,632 B1 | 7/2001 | Wu et al. |
| 6,257,706 B1 | 7/2001 | Ahn |
| 6,268,390 B1 | 7/2001 | Kunz |
| 6,273,908 B1 | 8/2001 | Ndondo-Lay |

| | | | | | | |
|---|---|---|---|---|---|---|
| 6,273,910 B1 | 8/2001 | Limon | 6,716,981 B2 | 4/2004 | Saikali et al. | |
| 6,273,913 B1 | 8/2001 | Wright et al. | 6,720,350 B2 | 4/2004 | Kunz et al. | |
| 6,280,411 B1 | 8/2001 | Lennox | 6,723,373 B1 | 4/2004 | Narayanan et al. | |
| 6,290,673 B1 | 9/2001 | Shanley | 6,730,064 B2 | 5/2004 | Ragheb et al. | |
| 6,293,967 B1 | 9/2001 | Shanley | 6,730,116 B1 | 5/2004 | Wolinsky et al. | |
| 6,299,604 B1 | 10/2001 | Ragheb et al. | 6,746,773 B2 | 6/2004 | Llanos et al. | |
| 6,299,755 B1 | 10/2001 | Richter | 6,752,829 B2 * | 6/2004 | Kocur et al. | 623/1.42 |
| 6,306,166 B1 | 10/2001 | Barry et al. | 6,753,071 B1 | 6/2004 | Pacetti | |
| 6,306,421 B1 | 10/2001 | Kunz et al. | 6,758,859 B1 | 7/2004 | Dang | |
| 6,309,414 B1 | 10/2001 | Rolando et al. | 6,764,507 B2 | 7/2004 | Shanley et al. | |
| 6,312,460 B2 | 11/2001 | Drasler et al. | 6,774,278 B1 | 8/2004 | Ragheb et al. | |
| 6,331,189 B1 | 12/2001 | Wolinsky et al. | 6,776,796 B2 | 8/2004 | Falotico et al. | |
| 6,334,807 B1 | 1/2002 | Lebel et al. | 6,780,424 B2 | 8/2004 | Claude | |
| 6,334,871 B1 | 1/2002 | Dor et al. | 6,783,543 B2 | 8/2004 | Jang | |
| 6,358,556 B1 | 3/2002 | Ding et al. | 6,783,793 B1 | 8/2004 | Hossainy et al. | |
| 6,358,989 B1 | 3/2002 | Kunz et al. | 6,790,228 B2 | 9/2004 | Hossainy | |
| 6,369,355 B1 | 4/2002 | Saunders | 6,805,898 B1 | 10/2004 | Wu et al. | |
| 6,375,826 B1 | 4/2002 | Wang et al. | 6,808,536 B2 | 10/2004 | Wright et al. | |
| 6,378,988 B1 | 4/2002 | Taylor et al. | 6,818,063 B1 | 11/2004 | Kerrigan | |
| 6,379,381 B1 | 4/2002 | Hossainy et al. | 6,846,841 B2 | 1/2005 | Hunter et al. | |
| 6,387,124 B1 | 5/2002 | Buscemi et al. | 6,849,089 B2 | 2/2005 | Stoll | |
| 6,395,326 B1 | 5/2002 | Castro et al. | 6,852,123 B2 | 2/2005 | Brown | |
| 6,399,144 B2 | 6/2002 | Dinh et al. | 6,855,125 B2 | 2/2005 | Shanley | |
| 6,403,635 B1 | 6/2002 | Kinsella et al. | 6,855,770 B2 | 2/2005 | Pinchuk et al. | |
| 6,423,092 B2 | 7/2002 | Datta et al. | 6,860,946 B2 | 3/2005 | Hossainy et al. | |
| 6,423,345 B2 | 7/2002 | Bernstein et al. | 6,861,088 B2 | 3/2005 | Weber et al. | |
| 6,429,232 B1 | 8/2002 | Kinsella et al. | 6,869,443 B2 | 3/2005 | Buscemi et al. | |
| 6,451,051 B2 | 9/2002 | Drasler et al. | 6,887,510 B2 | 5/2005 | Villareal | |
| 6,461,631 B1 | 10/2002 | Dunn et al. | 6,890,339 B2 | 5/2005 | Sahatjian et al. | |
| 6,475,237 B2 | 11/2002 | Drasler et al. | 6,896,965 B1 | 5/2005 | Hossainy | |
| 6,482,166 B1 | 11/2002 | Fariabi | 6,908,622 B2 | 6/2005 | Barry et al. | |
| 6,491,617 B1 | 12/2002 | Ogle et al. | 6,908,624 B2 | 6/2005 | Hossainy et al. | |
| 6,491,666 B1 | 12/2002 | Santini, Jr. et al. | 6,923,996 B2 | 8/2005 | Epstein et al. | |
| 6,491,938 B2 | 12/2002 | Kunz et al. | 6,926,919 B1 | 8/2005 | Hossainy et al. | |
| 6,497,916 B1 | 12/2002 | Taylor et al. | 6,929,660 B1 | 8/2005 | Ainsworth | |
| 6,500,859 B2 | 12/2002 | Kinsella et al. | 6,939,374 B2 | 9/2005 | Banik et al. | |
| 6,503,954 B1 | 1/2003 | Bhat et al. | 6,939,376 B2 | 9/2005 | Shulze et al. | |
| 6,506,411 B2 | 1/2003 | Hunter et al. | 6,953,560 B1 | 10/2005 | Castro et al. | |
| 6,506,437 B1 | 1/2003 | Harish et al. | 6,955,723 B2 | 10/2005 | Pacetti et al. | |
| 6,515,009 B1 | 2/2003 | Kunz et al. | 7,056,338 B2 | 6/2006 | Shanley et al. | |
| 6,528,121 B2 | 3/2003 | Yang et al. | 2001/0000802 A1 | 5/2001 | Soykan et al. | |
| 6,530,950 B1 | 3/2003 | Alvarado et al. | 2001/0018469 A1 | 8/2001 | Chen et al. | |
| 6,537,256 B2 | 3/2003 | Santini, Jr. et al. | 2001/0027291 A1 | 10/2001 | Shanley | |
| 6,544,544 B2 | 4/2003 | Hunter et al. | 2001/0027340 A1 | 10/2001 | Wright et al. | |
| 6,548,308 B2 | 4/2003 | Ellson et al. | 2001/0029351 A1 | 10/2001 | Falotico et al. | |
| 6,551,838 B2 | 4/2003 | Santini, Jr. et al. | 2001/0034363 A1 | 10/2001 | Li et al. | |
| 6,558,733 B1 | 5/2003 | Hossainy et al. | 2001/0044648 A1 | 11/2001 | Wolinsky et al. | |
| 6,562,065 B1 | 5/2003 | Shanley | 2001/0044652 A1 | 11/2001 | Moore | |
| 6,565,602 B2 | 5/2003 | Rolando et al. | 2002/0002400 A1 | 1/2002 | Drasler et al. | |
| 6,569,441 B2 | 5/2003 | Kunz et al. | 2002/0005206 A1 | 1/2002 | Falotico et al. | |
| 6,569,688 B2 | 5/2003 | Sivan et al. | 2002/0007209 A1 | 1/2002 | De Scheerder et al. | |
| 6,572,642 B2 | 6/2003 | Rinaldi et al. | 2002/0007213 A1 | 1/2002 | Falotico et al. | |
| 6,585,764 B2 | 7/2003 | Wright et al. | 2002/0007214 A1 | 1/2002 | Falotico | |
| 6,585,765 B1 | 7/2003 | Hossainy et al. | 2002/0007215 A1 | 1/2002 | Falotico et al. | |
| 6,585,773 B1 | 7/2003 | Xie | 2002/0010507 A1 | 1/2002 | Ehr et al. | |
| 6,599,415 B1 | 7/2003 | Ku et al. | 2002/0013619 A1 | 1/2002 | Shanley | |
| 6,599,928 B2 | 7/2003 | Kunz et al. | 2002/0016625 A1 | 2/2002 | Falotico et al. | |
| 6,613,084 B2 | 9/2003 | Yang | 2002/0022876 A1 | 2/2002 | Richter et al. | |
| 6,616,765 B1 | 9/2003 | Castro et al. | 2002/0028243 A1 | 3/2002 | Masters | |
| 6,627,246 B2 | 9/2003 | Mehta et al. | 2002/0032414 A1 | 3/2002 | Ragheb et al. | |
| 6,635,082 B1 | 10/2003 | Hossainy et al. | 2002/0038145 A1 | 3/2002 | Jang | |
| 6,638,302 B1 | 10/2003 | Curcio et al. | 2002/0038146 A1 | 3/2002 | Harry | |
| 6,645,547 B1 | 11/2003 | Shekalim et al. | 2002/0068969 A1 | 6/2002 | Shanley et al. | |
| 6,656,162 B2 | 12/2003 | Santini et al. | 2002/0071902 A1 | 6/2002 | Ding et al. | |
| 6,656,217 B1 | 12/2003 | Herzog et al. | 2002/0072511 A1 | 6/2002 | New et al. | |
| 6,660,034 B1 | 12/2003 | Mandrusov et al. | 2002/0082679 A1 | 6/2002 | Sirhan et al. | |
| 6,663,881 B2 | 12/2003 | Kunz et al. | 2002/0082680 A1 | 6/2002 | Shanley et al. | |
| 6,673,385 B1 | 1/2004 | Ding et al. | 2002/0082682 A1 | 6/2002 | Barclay et al. | |
| 6,676,987 B2 | 1/2004 | Zhong et al. | 2002/0094985 A1 | 7/2002 | Herrmann | |
| 6,679,980 B1 | 1/2004 | Andreacchi | 2002/0107563 A1 | 8/2002 | Shanley | |
| 6,682,545 B1 | 1/2004 | Kester | 2002/0123801 A1 | 9/2002 | Pacetti et al. | |
| 6,682,771 B2 | 1/2004 | Zhong et al. | 2002/0127263 A1 | 9/2002 | Carlyle et al. | |
| 6,689,159 B2 | 2/2004 | Lau et al. | 2002/0128704 A1 | 9/2002 | Daum et al. | |
| 6,689,390 B2 | 2/2004 | Bernstein et al. | 2002/0142039 A1 | 10/2002 | Claude | |
| 6,699,281 B2 | 3/2004 | Vallana et al. | 2002/0155212 A1 | 10/2002 | Hossainy | |
| 6,702,850 B1 | 3/2004 | Byun et al. | 2002/0165604 A1 | 11/2002 | Shanley | |
| 6,712,845 B2 | 3/2004 | Hossainy | 2002/0193475 A1 | 12/2002 | Hossainy et al. | |
| 6,713,119 B2 | 3/2004 | Hossainy et al. | 2003/0004141 A1 | 1/2003 | Brown | |
| 6,716,444 B1 | 4/2004 | Castro et al. | 2003/0009214 A1 | 1/2003 | Shanley | |

| Pub. No. | Date | Inventor |
|---|---|---|
| 2003/0022542 A1 | 1/2003 | Nakamura |
| 2003/0028243 A1 | 2/2003 | Bates et al. |
| 2003/0028244 A1 | 2/2003 | Bates et al. |
| 2003/0033007 A1 | 2/2003 | Sirhan et al. |
| 2003/0036794 A1 | 2/2003 | Ragheb et al. |
| 2003/0050687 A1 | 3/2003 | Schwade et al. |
| 2003/0060877 A1 | 3/2003 | Falotico et al. |
| 2003/0068355 A1* | 4/2003 | Shanley et al. ............... 424/426 |
| 2003/0069606 A1 | 4/2003 | Girouard et al. |
| 2003/0072783 A1* | 4/2003 | Stamler et al. ............... 424/423 |
| 2003/0077312 A1 | 4/2003 | Schmulewicz et al. |
| 2003/0083646 A1 | 5/2003 | Sirhan et al. |
| 2003/0086957 A1 | 5/2003 | Hughes et al. |
| 2003/0088307 A1 | 5/2003 | Shulze et al. |
| 2003/0100865 A1 | 5/2003 | Santini et al. |
| 2003/0125800 A1 | 7/2003 | Shulze et al. |
| 2003/0125803 A1 | 7/2003 | Vallana et al. |
| 2003/0157241 A1 | 8/2003 | Hossainy et al. |
| 2003/0167085 A1 | 9/2003 | Shanley |
| 2003/0176915 A1 | 9/2003 | Wright et al. |
| 2003/0181973 A1 | 9/2003 | Sahota |
| 2003/0199970 A1 | 10/2003 | Shanley |
| 2003/0204239 A1 | 10/2003 | Carlyle et al. |
| 2003/0216699 A1 | 11/2003 | Falotico |
| 2004/0000638 A1 | 1/2004 | Lorusso |
| 2004/0024449 A1 | 2/2004 | Boyle |
| 2004/0073294 A1* | 4/2004 | Diaz et al. ............... 623/1.42 |
| 2004/0073296 A1 | 4/2004 | Epstein et al. |
| 2004/0098117 A1 | 5/2004 | Hossainy et al. |
| 2004/0122505 A1 | 6/2004 | Shanley |
| 2004/0122506 A1 | 6/2004 | Shanley et al. |
| 2004/0127976 A1 | 7/2004 | Diaz |
| 2004/0127977 A1 | 7/2004 | Shanley |
| 2004/0142014 A1 | 7/2004 | Litvack et al. |
| 2004/0143321 A1 | 7/2004 | Litvack et al. |
| 2004/0143322 A1 | 7/2004 | Litvack et al. |
| 2004/0166140 A1 | 8/2004 | Santini et al. |
| 2004/0193255 A1 | 9/2004 | Shanley et al. |
| 2004/0202692 A1 | 10/2004 | Shanley et al. |
| 2004/0204756 A1 | 10/2004 | Diaz et al. |
| 2004/0208985 A1 | 10/2004 | Rowan et al. |
| 2004/0220660 A1 | 11/2004 | Shanley et al. |
| 2004/0220665 A1 | 11/2004 | Hossainy et al. |
| 2004/0225350 A1 | 11/2004 | Shanley |
| 2004/0234737 A1 | 11/2004 | Pacetti |
| 2004/0249449 A1 | 12/2004 | Shanley et al. |
| 2005/0038505 A1 | 2/2005 | Shulze et al. |
| 2005/0049693 A1 | 3/2005 | Walker |
| 2005/0055078 A1 | 3/2005 | Campbell |
| 2005/0058684 A1 | 3/2005 | Shanley et al. |
| 2005/0059991 A1 | 3/2005 | Shanley |
| 2005/0060020 A1 | 3/2005 | Jenson |
| 2005/0064088 A1 | 3/2005 | Fredrickson |
| 2005/0074545 A1 | 4/2005 | Thomas |
| 2005/0075714 A1 | 4/2005 | Cheng et al. |
| 2005/0079199 A1 | 4/2005 | Heruth et al. |
| 2005/0084515 A1 | 4/2005 | Udipi et al. |
| 2005/0100577 A1 | 5/2005 | Parker et al. |
| 2005/0106210 A1 | 5/2005 | Ding et al. |
| 2005/0113903 A1 | 5/2005 | Rosenthal et al. |
| 2005/0119720 A1 | 6/2005 | Gale et al. |
| 2005/0158360 A1 | 7/2005 | Falotico et al. |
| 2005/0169969 A1 | 8/2005 | Li et al. |
| 2005/0177226 A1 | 8/2005 | Banik et al. |
| 2005/0187611 A1 | 8/2005 | Ding et al. |
| 2005/0197691 A1 | 9/2005 | Hezi-Yamit et al. |
| 2005/0208200 A1 | 9/2005 | Ding et al. |
| 2005/0233062 A1 | 10/2005 | Hossainy et al. |
| 2005/0234538 A1 | 10/2005 | Litvack et al. |
| 2005/0234544 A1 | 10/2005 | Shanley |
| 2005/0251248 A1 | 11/2005 | Chandresekara et al. |
| 2005/0256564 A1 | 11/2005 | Yang et al. |
| 2005/0261762 A1 | 11/2005 | Hezi-Yamit |
| 2005/0271697 A1 | 12/2005 | Litvack |
| 2005/0273161 A1 | 12/2005 | Malik et al. |
| 2005/0278016 A1 | 12/2005 | Welsh et al. |
| 2006/0009838 A1 | 1/2006 | Shanley et al. |
| 2006/0035879 A1 | 2/2006 | Prescott |
| 2006/0064157 A1 | 3/2006 | Shanley |
| 2006/0122688 A1 | 6/2006 | Shanley et al. |
| 2006/0178734 A1 | 8/2006 | Parker et al. |
| 2006/0178735 A1 | 8/2006 | Litvack et al. |

FOREIGN PATENT DOCUMENTS

| | | |
|---|---|---|
| EP | 294905 | 12/1988 |
| EP | 294905 A1 | 12/1988 |
| EP | 335341 A1 | 10/1989 |
| EP | 375520 A1 | 6/1990 |
| EP | 470246 | 2/1992 |
| EP | 470569 A1 | 2/1992 |
| EP | 540290 A2 | 5/1993 |
| EP | 543653 | 5/1993 |
| EP | 551182 | 7/1993 |
| EP | 566245 | 10/1993 |
| EP | 567816 A1 | 11/1993 |
| EP | 568310 | 11/1993 |
| EP | 604022 | 6/1994 |
| EP | 623354 | 11/1994 |
| EP | 627226 | 12/1994 |
| EP | 679373 | 11/1995 |
| EP | 706376 | 4/1996 |
| EP | 716836 | 6/1996 |
| EP | 809515 | 8/1996 |
| EP | 734698 A2 | 10/1996 |
| EP | 734699 B1 | 10/1996 |
| EP | 747069 | 12/1996 |
| EP | 752885 | 1/1997 |
| EP | 770401 A2 | 5/1997 |
| EP | 797963 | 10/1997 |
| EP | 807424 A2 | 11/1997 |
| EP | 832655 | 4/1998 |
| EP | 875218 | 4/1998 |
| EP | 850651 | 7/1998 |
| EP | 897700 A1 | 2/1999 |
| EP | 950386 | 10/1999 |
| EP | 1118325 | 7/2001 |
| EP | 1132058 | 9/2001 |
| EP | 1172074 | 1/2002 |
| EP | 1181943 | 2/2002 |
| EP | 1222941 | 7/2002 |
| EP | 1223305 A2 | 7/2002 |
| EP | 1236478 | 9/2002 |
| EP | 1277449 | 1/2003 |
| EP | 711158 | 3/2003 |
| EP | 1155690 | 9/2004 |
| EP | 975340 | 10/2004 |
| EP | 1470828 | 10/2004 |
| EP | 1479401 | 10/2004 |
| EP | 1472992 | 11/2004 |
| EP | 959812 | 1/2005 |
| EP | 1493456 | 1/2005 |
| EP | 1493457 | 1/2005 |
| EP | 1500406 | 1/2005 |
| EP | 1500407 | 1/2005 |
| EP | 980280 | 2/2005 |
| EP | 1181903 | 2/2005 |
| EP | 1504775 | 2/2005 |
| EP | 1518570 | 3/2005 |
| EP | 1527754 | 5/2005 |
| EP | 1557183 | 7/2005 |
| EP | 1559439 | 8/2005 |
| EP | 1566187 | 8/2005 |
| EP | 1570871 | 9/2005 |
| EP | 1574228 | 9/2005 |
| EP | 1330993 | 10/2005 |
| EP | 1341479 | 10/2005 |
| EP | 1561436 A1 | 10/2005 |
| EP | 1582180 | 10/2005 |
| EP | 1582225 | 10/2005 |
| EP | 1586338 | 10/2005 |
| EP | 1588725 | 10/2005 |
| EP | 1588726 | 10/2005 |
| EP | 1588727 | 10/2005 |
| EP | 1600123 | 11/2005 |
| EP | 1600180 | 11/2005 |
| FR | 2764794 A1 | 12/1998 |
| WO | WO-9001969 | 3/1990 |
| WO | WO-9013332 | 11/1990 |

| | | |
|---|---|---|
| WO | WO 9110424 A1 | 7/1991 |
| WO | WO 9111193 A1 | 8/1991 |
| WO | WO 9112779 A1 | 9/1991 |
| WO | WO-9112779 | 11/1991 |
| WO | WO-9200747 | 1/1992 |
| WO | WO 9215286 A1 | 9/1992 |
| WO | WO 9212717 A3 | 10/1992 |
| WO | WO-9306792 | 4/1993 |
| WO | WO-9311120 | 6/1993 |
| WO | WO-9407529 | 4/1994 |
| WO | WO-9413268 | 6/1994 |
| WO | WO-9416706 | 8/1994 |
| WO | WO-9421308 | 9/1994 |
| WO | WO-9424961 | 11/1994 |
| WO | WO-9424962 | 11/1994 |
| WO | WO-9503036 | 2/1995 |
| WO | WO-9503795 | 2/1995 |
| WO | WO-9524908 | 9/1995 |
| WO | WO 9524908 A1 | 9/1995 |
| WO | WO 9603092 A1 | 2/1996 |
| WO | WO-9625176 | 8/1996 |
| WO | WO 9629028 A1 | 9/1996 |
| WO | WO-9632907 | 10/1996 |
| WO | WO 9632907 A1 | 10/1996 |
| WO | WO 9704721 A1 | 2/1997 |
| WO | WO-9710011 | 3/1997 |
| WO | WO 9808566 A1 | 3/1998 |
| WO | WO 9818407 A1 | 5/1998 |
| WO | WO 9819628 A1 | 5/1998 |
| WO | WO-9823228 | 6/1998 |
| WO | WO-9823244 | 6/1998 |
| WO | WO-9836784 | 8/1998 |
| WO | WO 9858600 A1 | 12/1998 |
| WO | WO 9915108 A2 | 4/1999 |
| WO | WO-9916386 | 4/1999 |
| WO | WO-9916477 | 4/1999 |
| WO | WO9923977 A1 | 5/1999 |
| WO | WO 9944536 A1 | 9/1999 |
| WO | WO-9949928 | 10/1999 |
| WO | WO 9949928 A1 | 10/1999 |
| WO | WO-9955396 | 11/1999 |
| WO | WO 0010613 A2 | 3/2000 |
| WO | WO-0010622 | 3/2000 |
| WO | WO-0045744 | 8/2000 |
| WO | WO 0069368 A2 | 11/2000 |
| WO | WO-0071054 | 11/2000 |
| WO | WO-0110421 | 2/2001 |
| WO | WO-0117577 | 3/2001 |
| WO | WO-0145763 | 6/2001 |
| WO | WO 0145862 A1 | 6/2001 |
| WO | WO-0149338 | 7/2001 |
| WO | WO-0152915 | 7/2001 |
| WO | WO-0187376 | 11/2001 |
| WO | WO2004096176 A2 | 11/2001 |
| WO | WO-0217880 | 3/2002 |
| WO | WO-0226162 | 4/2002 |
| WO | WO-0226281 | 4/2002 |
| WO | WO-0232347 | 4/2002 |
| WO | WO 02/41931 A3 | 5/2002 |
| WO | WO-0241931 A2 | 5/2002 |
| WO | WO-0243788 | 6/2002 |
| WO | WO02055121 A1 | 7/2002 |
| WO | WO02055122 A1 | 7/2002 |
| WO | WO-02060506 | 8/2002 |
| WO | WO-02087586 | 11/2002 |
| WO | WO-03015664 | 2/2003 |
| WO | WO-03018083 | 3/2003 |
| WO | WO-03035132 | 5/2003 |
| WO | WO-03082364 | 10/2003 |
| WO | WO-03082368 | 10/2003 |
| WO | WO-04000379 | 12/2003 |
| WO | WO-2004043510 | 5/2004 |
| WO | WO-2004043511 | 5/2004 |
| WO | WO-2004045578 | 6/2004 |
| WO | WO2004087015 A2 | 10/2004 |
| WO | WO-2004091714 | 10/2004 |
| WO | WO-2004096311 | 11/2004 |
| WO | WO-2004098451 | 11/2004 |
| WO | WO-2004098671 | 11/2004 |
| WO | WO-2004101018 | 11/2004 |
| WO | WO-2004103428 | 12/2004 |
| WO | WO-2005000939 | 1/2005 |
| WO | WO-2005004945 | 1/2005 |
| WO | WO-2005004946 | 1/2005 |
| WO | WO-2005007035 | 1/2005 |
| WO | WO-2005011766 | 2/2005 |
| WO | WO-2005011767 | 2/2005 |
| WO | WO-2005011769 | 2/2005 |
| WO | WO-2005011770 | 2/2005 |
| WO | WO-2005016187 | 2/2005 |
| WO | WO-2005016396 | 2/2005 |
| WO | WO-2005018606 | 3/2005 |
| WO | WO-2005027794 | 3/2005 |
| WO | WO-2005034805 | 4/2005 |
| WO | WO-2005034806 | 4/2005 |
| WO | WO-2005037444 | 4/2005 |
| WO | WO-2005037447 | 4/2005 |
| WO | WO-2005040416 | 5/2005 |
| WO | WO-2005044506 | 5/2005 |
| WO | WO-2005046521 | 5/2005 |
| WO | WO-2005049678 | 6/2005 |
| WO | WO-2005051449 | 6/2005 |
| WO | WO-2005053571 | 6/2005 |
| WO | WO-2005053937 | 6/2005 |
| WO | WO-2005082283 | 9/2005 |
| WO | WO-2005089824 | 9/2005 |
| WO | WO-2005089825 | 9/2005 |
| WO | WO-2005092242 | 10/2005 |
| WO | WO-2005092406 | 10/2005 |
| WO | WO-2005094930 | 10/2005 |
| WO | WO-2005097066 | 10/2005 |
| WO | WO-2005097220 | 10/2005 |
| WO | WO-2005112570 | 12/2005 |
| WO | WO2005115277 A2 | 12/2005 |
| WO | WO-2005120397 | 12/2005 |
| WO | WO-2006007473 | 1/2006 |
| WO | WO2006012034 A2 | 2/2006 |
| WO | WO-2006012060 | 2/2006 |
| WO | WO03020329 A1 | 3/2006 |
| WO | WO-2006036319 | 4/2006 |
| WO | WO-2005089951 | 9/2009 |

OTHER PUBLICATIONS

Ruaraidh A. Hill, et al. "Drug-eluting Stents: an Early Systematic Review to Inform Policy." European Heart Journal (2004) 25, 902-919.

William L. Hunter, et al., Local Delivery of Chemotherapy: A Supplement to Existing Cancer Treatments a Case for Surgical Pastes and Coated Stents, Elseriver Science, 069-409X/1997.

P.W. Serruys, et al., The Effect of Variale Dose and Release Kinetics on Neointimal Hyperplasia Using a Novel Paclitaxel-Eluting Stent Platform, Journal of the American College of Cardiology, vol. 46, No. 2, 2005.

Steven R. Bailey, et al., Coating of Endovascular Stents, Textbook of Interventional Cardiology, 1994.

Dorin Panescu, "Drug Eluting Stents," IEEE Engineering in Medicine and Biology Magazine, Mar./Apr. 2004.

Georgina M. Nemecek, et al., "Terbinafine Inhibits the Mitogenic Response to Platelet-Derived Growth Factor in Vitro and Neointimal Proliferation in Vivo," The Journal of Pharmacology and Experimental Therapeutics, vol. 248, No. 3. 1987.

J. Eduardo Sousa, et al., New Frontiers in Cardiology Drug-Eluting Stents: Part I, Circulation, 2003; 107:2274-2279.

Manfred Boehm, et al., "Cell Cycle and Cell Migration: New Pieces to the Puzzle," Circulation 2001;103:2879-2881.

Ruediger C. Braun-Dullaeus, et al., "Cell Cycle Progression: New Therapeutic Target for Vascular Proliferative Disease," Circulation. 1998;98:82-89.

Eric J. Topol, et al., "Frontiers in Interventional Cardiology," Circulation. 1998;98:1802-1820.

Babapulle, et al., Coated Stents for the Prevention of Restenosis: Part II, Circulation, Nov. 26, 2002.

Stone, et al., One Year Clinical Results with the Slow-Release, Polymer-Based, Padlitaxel-Eluting TAXUS Stent, Circulation, Apr. 27, 2004.

Moussa, et al., Impact of Sirolimus-Eluting Stents on Outcome in Diabetic Patients, Circulation, May 18, 2004.

Sriram, et al., Cell Cycle in Vasculoproliferative Diseases, May 15, 2001.

Kereiakes, et al., Hipporates Revisited, The Evidence for Drug-Eluting Stents, Circulation, Jun. 24, 2003.

Suzuki, et al., Stent-Based Delivery of Sirolimus Reduces Neointimal Formation in a Porcine Cornonary Model, Circulation, Sep. 4, 2001.

Morice, et al., The Ravel Trial, Evidence-Based Medecine.

* cited by examiner

IMPLANTABLE MEDICAL DEVICE WITH BENEFICIAL AGENT CONCENTRATION GRADIENT

CROSS REFERENCE TO RELATED APPLICATIONS

This application is a Divisional of U.S. patent application Ser. No. 10/777,283, filed Feb. 11, 2004, which is a Continuation-in-Part of U.S. patent application Ser. No. 10/402,893 filed on Mar. 28, 2003, which is incorporated herein by reference in its entirety.

FIELD OF THE INVENTION

The invention relates to a therapeutic agent delivery device which has a concentration gradient of the therapeutic agent contained within a matrix to provide release kinetics which are specifically programmable for the particular agent, administration period, and release rate desired.

BACKGROUND

Implantable medical devices are sometimes used for delivery of a therapeutic agent, such as a drug, to an organ or tissue in the body. It is hoped that these devices may deliver agents to a wide variety of bodily systems to provide a wide variety of treatments.

One implantable medical device which has been used for local delivery of therapeutic agents is the coronary stent. Coronary stents are typically introduced percutaneously, and transported transluminally until positioned at a desired location. These devices are then expanded either mechanically, such as by the expansion of a mandrel or balloon positioned inside the device, or expand themselves by releasing stored energy upon actuation within the body. Once expanded within the lumen, these devices, called stents, become encapsulated within the body tissue and remain a permanent implant.

Of the many problems that may be addressed through stent-based local delivery of therapeutic agents, one of the most important is restenosis. Restenosis is a major complication that can arise following vascular interventions such as angioplasty and the implantation of stents. Simply defined, restenosis is a wound healing process that reduces the vessel lumen diameter by extracellular matrix deposition, neointimal hyperplasia, and vascular smooth muscle cell proliferation, and which may ultimately result in renarrowing or even reocclusion of the lumen. Despite the introduction of improved surgical techniques, devices, and pharmaceutical agents, the overall restenosis rate is still reported in the range of 25% to 50% within six to twelve months after an angioplasty procedure. To treat this condition, additional revascularization procedures are frequently required, thereby increasing trauma and risk to the patient.

One of the techniques under development to address the problem of restenosis is the use of surface coatings of various therapeutic agents on stents. U.S. Pat. No. 5,716,981, for example, discloses a stent that is surface-coated with a composition comprising a polymer carrier and paclitaxel (a well-known compound that is commonly used in the treatment of cancerous tumors). Known surface coatings, however, can provide little actual control over the release kinetics of therapeutic agents. These coatings are generally very thin, typically 5 to 8 microns deep. The surface area of the stent, by comparison is very large, so that the entire volume of the therapeutic agent has a very short diffusion path to discharge into the surrounding tissue. The ability to shape the release profiles from such systems is severely limited.

Accordingly, it would be desirable to provide a therapeutic agent delivery device with the ability to program the release kinetics to the particular agent, administration period, and release rate desired.

SUMMARY OF THE INVENTION

The present invention relates to implantable medical devices for programmable delivery of a therapeutic agent, methods of forming implantable medical devices, and methods for delivering therapeutic agents from implantable medical devices.

In accordance with one aspect of the invention, an implantable medical device configured to release at least one therapeutic agent therefrom is provided, wherein the device includes an implantable body and a matrix affixed to the implantable body. The matrix contains the at least one therapeutic agent therein, and the matrix is formed such that the concentration of the therapeutic agent in the matrix varies as a continuous gradient relative to a surface of the implantable body.

In accordance with another aspect of the invention, a method of forming an implantable medical device configured to release at least one therapeutic agent therefrom is provided. The therapeutic agent is disposed in a matrix affixed to the body of the implantable medical device, and the concentration of the at least one therapeutic agent in the matrix varies as a continuous gradient relative to a surface of the body of the implantable medical device. The method involves forming a first homogeneous solution comprising the at least one therapeutic agent mixed with a polymeric binder, applying the first homogeneous solution to the body of the implantable medical device, solidifying the first homogeneous solution, thereby forming a first portion of the matrix, forming a second homogeneous solution comprising the polymeric binder, applying the second homogeneous solution to the first portion of the matrix, thereby at least partially liquifying the first portion of the matrix, and solidifying the second homogeneous solution, thereby forming a second portion of the matrix, wherein the concentration of the at least one therapeutic agent in the matrix is different in the first and second portions of the matrix.

In accordance with an additional aspect of the invention, a method of forming an implantable medical device configured to release at least one therapeutic agent therefreom is provided. The therapeutic agent is disposed in a matrix affixed to a body of the implantable medical device, and a concentration of the at least one therapeutic agent in the matrix varies as a continuous gradient relative to a surface of the implantable medical device body. The method involves forming a homogeneous solution comprising a polymeric binder and a solvent, evaporating the solvent in the homogeneous solution, thereby forming a matrix, exposing the matrix to a solution comprising the therapeutic agent for a time sufficient to produce a partial diffusion of the therapeutic agent into the matrix such that the concentration of the therapeutic agent varies in the matrix, and affixing the matrix to the implantable medical device body.

In accordance with a further aspect of the invention, a method for treating a patient by local delivery of at least one therapeutic agent is provided. The method involves delivering an inplantable medical device into the body of a patient, the implantable medical device having a matrix affixed to a body of the implantable medical device with concentration of the at least one therapeutic agent in the matrix varying as a continuous gradient relative to a surface of the body of the implantable medical device. The method further involves delivering the therapeutic agent at a release rate and over an administration period determined by the gradient of therapeutic agent in the matrix.

BRIEF DESCRIPTION OF THE DRAWINGS

The invention will now be described in greater detail with reference to the preferred embodiments illustrated in the accompanying drawings, in which like elements bear like reference numerals, and wherein.

DETAILED DESCRIPTION

Figure 1:
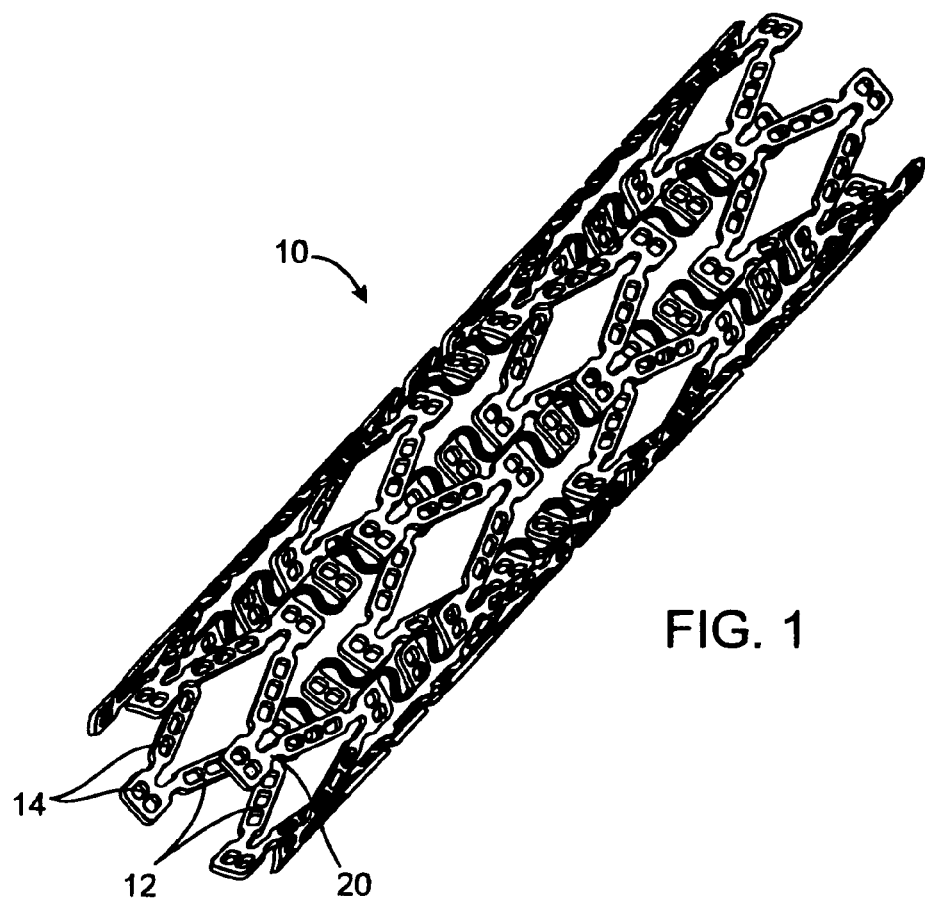
FIG. 1 is a perspective view of one example of a stent according to the present invention.

The invention relates to a medical device or stent having a matrix containing a therapeutic agent therein such that the concentration of agent in the matrix varies as a function of the position relative to the matrix surfaces. The agent may be any therapeutic agent that provides a beneficial effect after the deployment of the medical device and release of the agent from the matrix into the tissue of a mammal.

First, the following terms, as used herein, shall have the following meanings:

The terms "drug" and "therapeutic agent" are used interchangeably to refer to any therapeutically active substance that is delivered to a living being to produce a desired, usually beneficial, effect.

The term "matrix" or "biocompatible matrix" are used interchangeably to refer to a medium or material that, upon implantation in a subject, does not elicit a detrimental response sufficient to result in the rejection of the matrix. The matrix typically does not provide any therapeutic responses itself, though the matrix may contain or surround a therapeutic agent, and/or modulate the release of the therapeutic agent into the body. A matrix is also a medium that may simply provide support, structural integrity or structural barriers. The matrix may be polymeric, non-polymeric, hydrophobic, hydrophilic, lipophilic, amphiphilic, and the like. The matrix may be bioresorbable or non-bioresorbable.

The term "bioresorbable" refers to a matrix, as defined herein, that can be broken down by either chemical or physical process, upon interaction with a physiological environment. The matrix can erode or dissolve. A bioresorbable matrix serves a temporary function in the body, such as drug delivery, and is then degraded or broken into components that are metabolizable or excretable, over a period of time from minutes to years, preferably less than one year, while maintaining any requisite structural integrity in that same time period.

The term "openings" includes both through openings and recesses.

The term "pharmaceutically acceptable" refers to the characteristic of being non-toxic to a host or patient and suitable for maintaining the stability of a therapeutic agent and allowing the delivery of the therapeutic agent to target cells or tissue.

The term "polymer" refers to molecules formed from the chemical union of two or more repeating units, called monomers. Accordingly, included within the term "polymer" may be, for example, dimers, trimers and oligomers. The polymer may be synthetic, naturally-occurring or semisynthetic. In preferred form, the term "polymer" refers to molecules which typically have a $M_W$ greater than about 3000 and preferably greater than about 10,000 and a $M_W$ that is less than about 10 million, preferably less than about a million and more preferably less than about 200,000. Examples of polymers include but are not limited to, poly-α-hydroxy acid esters such as, polylactic acid (PLLA or DLPLA), polyglycolic acid, polylactic-co-glycolic acid (PLGA), polylactic acid-co-caprolactone; poly (block-ethylene oxide-block-lactide-co-glycolide) polymers (PEO-block-PLGA and PEO-block-PLGA-block-PEO); polyethylene glycol and polyethylene oxide, poly (block-ethylene oxide-block-propylene oxide-block-ethylene oxide); polyvinyl pyrrolidone; polyorthoesters; polysaccharides and polysaccharide derivatives such as polyhyaluronic acid, poly (glucose), polyalginic acid, chitin, chitosan, chitosan derivatives, cellulose, methyl cellulose, hydroxyethylcellulose, hydroxypropylcellulose, carboxymethylcellulose, cyclodextrins and substituted cyclodextrins, such as beta-cyclodextrin sulfobutyl ethers; polypeptides and proteins, such as polylysine, polyglutamic acid, albumin; polyanhydrides; polyhydroxy alkonoates such as polyhydroxy valerate, polyhydroxy butyrate, and the like.

The term "primarily" with respect to directional delivery, refers to an amount greater than about 50% of the total amount of therapeutic agent provided to a blood vessel.

The term "restenosis" refers to the renarrowing of an artery following an angioplasty procedure which may include stenosis following stent implantation.

The term "liquefied" is used herein to define a component which is put in a liquid state either by heating the component to a temperature higher than its melting point, or glass transition temperature, or by dissolving the component in a solvent. The typical liquefied materials of the present invention will have a viscosity of less than about 10,000 centipoise, and preferably less than about 1,000 centipoise, and more preferably less than about 100 centipoise.

The term "homogeneously disposed" refers to a mixture in which each of the components are uniformly dispersed within the matrix.

The term "heterogeneously disposed" refers to a mixture in which the components are not mixed uniformly into a matrix.

FIG. 1 illustrates one example of an implantable medical device in the form of a stent 10. Although the present invention will be described with reference to a stent, the invention can also be useful as other types of drug delivery implants including subcutaneous implants, embolization devices, and implants for delivery of chemotherapeutic agents.

Figure 2:
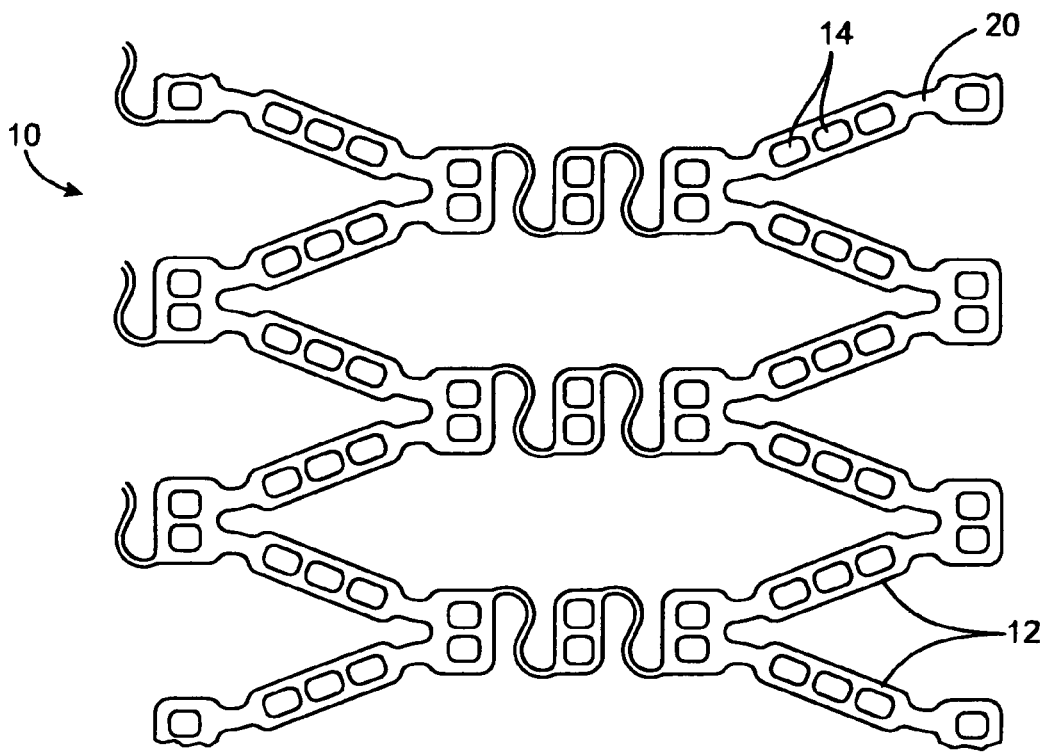
FIG. 2 is a side view of a portion of the stent of FIG. 1.

FIG. 2 is an enlarged flattened view of a portion of the stent of FIG. 1 illustrating one example of a stent structure including struts 12 interconnected by ductile hinges 20. The struts 12 include openings 14 which can be non-deforming openings containing the therapeutic agent and matrix. One example of a stent structure having non-deforming openings is shown in U.S. Pat. No. 6,562,065 which is incorporated herein by reference in its entirety.

The implantable medical devices of the present invention are configured to release at least one therapeutic agent from a matrix affixed to the implantable body. The matrix is formed such that the concentration of the therapeutic agent in the matrix varies as a gradient relative to a surface of the matrix affixed to the implantable body. The deposition of a coating on a surface, such as by dipping or spraying may result in the phenomenon know as blooming by which the drug migrates to the surface resulting in increased concentration at the matrix surface. However, known coating methods do not achieve configurations in which a concentration in an area adjacent the matrix surface is less than a concentration of the drug at another part of the matrix. The present invention provides methods and devices by which an implantable medical device can be designed to achieve a particular release profile by providing a concentration gradient of drug in a homogeneous polymer matrix in which the concentration gradient is provided other than by the phenomenon of blooming.

In one embodiment, the matrix is a polymeric material which acts as a binder or carrier to hold the agent in or on the stent and/or modulate the release of the agent from the stent. The polymeric material can be a bioresorbable or a non-bioresorbable material.

The therapeutic agent containing matrix can be disposed in the stent or on surfaces of the stent in various configurations, including within volumes defined by the stent, such as openings, holes, or concave surfaces, as a reservoir of agent, and alternatively as a coating on all or a portion of surfaces of the stent structure. When the therapeutic agent matrix is disposed within openings in the strut structure of the stent to form a reservoir, the openings may be partially or completely filled with matrix containing the therapeutic agent.

The concentration of agent in a local region of the matrix is the sum of the amount of agent dissolved in the matrix, in a so-called solid solution morphology, and the amount dispersed in that local region of the matrix, a so-called solid emulsion morphology. The relative amount of dissolved and dispersed agent in a region is controlled by the solubility of the agent in the matrix material. When the limit of solubility of the agent in the matrix material is reached, any additional agent will be in a dispersed second phase particulate morphology.

Figure 3:
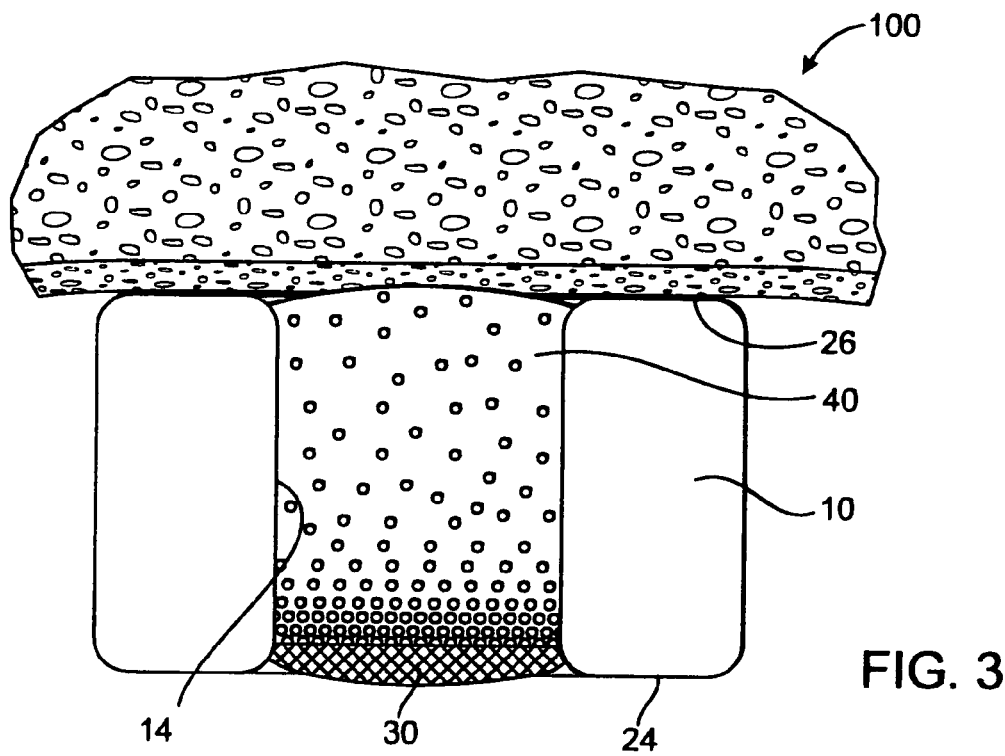
FIG. 3 is a side cross sectional view of an example of an opening in a stent showing a matrix with one therapeutic agent having a concentration gradient.

FIG. 3 is a cross section of the stent 10 and blood vessel 100 illustrating one example of an opening 14 arranged adjacent the vessel wall with a mural surface 26 abutting the vessel wall and a luminal surface 24 opposite the mural surface. The opening 14 of FIG. 3 contains a matrix 40 with a therapeutic agent illustrated by Os in the matrix. As can be seen in the example of FIG. 3, the concentration of the therapeutic agent (Os) is highest at the luminal side of the matrix 40 and lowest at the mural side of the matrix. The luminal side 24 of the stent 10 is also provided with a barrier layer 30. The barrier layer 30 causes the therapeutic agent to be delivered primarily to the mural side 26 of the stent.

Figure 4:
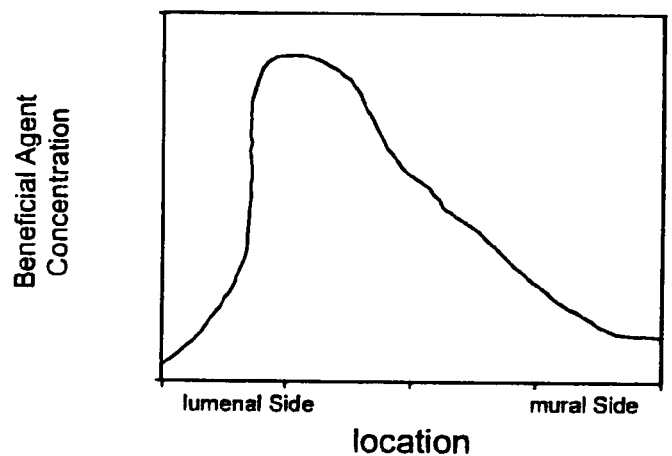
FIG. 4 is a graph of the therapeutic agent concentration gradient of FIG. 3.

FIG. 4 illustrates graphically a concentration gradient similar to that depicted in FIG. 3 where the agent concentration in the matrix is highest in the middle of the stent or adjacent the luminally located barrier layer 30 and the agent concentration decreases moving toward the mural side of the matrix. The concentration gradient is described by the local concentration of the agent in matrix regions along a theoretical line substantially perpendicular to the surfaces of the matrix. A continuous agent concentration gradient is where the agent concentration in a volume of matrix varies in a blended fashion in moving between successive positions along the line substantially perpendicular to the matrix surface. Thus, if the matrix surface was substantially collinear with the stent surface and the matrix was sliced into a plurality of slices substantially parallel to the stent surface, the adjacent slices will have different agent concentrations. Alternately, the matrix surface may be contoured and the adjacent slices may be similarly configured.

As illustrated in FIG. 3, the barrier layer 30 includes no therapeutic agent and the concentration gradient of therapeutic agent is provided in the matrix in the portion of the opening 14 not containing the barrier material. Alternatively, the barrier layer 30 may include some therapeutic agent and the concentration gradient may continue in part or all of the barrier layer.

Figure 5:
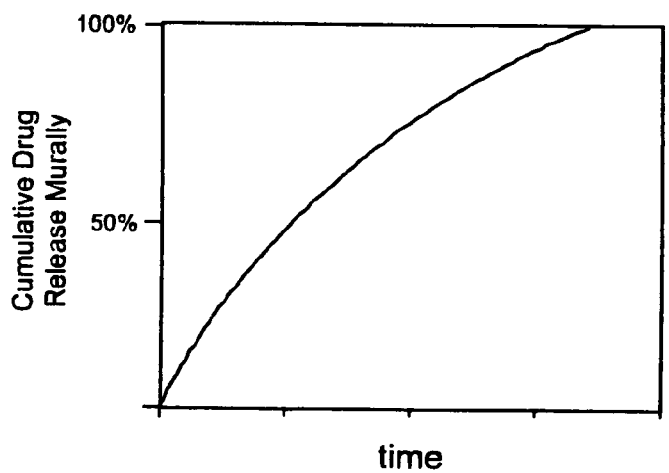
FIG. 5 is a graph of the release kinetics of the stent of FIG. 3.

As shown in FIG. 4, the change in agent concentration in the matrix is a continuous function of the position relative to the matrix surfaces. As shown in FIG. 5, the release kinetics of the system of FIGS. 3 and 4 can be essentially linear (essentially constant release rate over time) after an initial release. Such substantially linear release profiles are described in further detail in U.S. patent application Ser. No. 10/777,881 filed on Feb. 11, 2004 which is incorporated herein by reference in its entirety.

Figure 6:
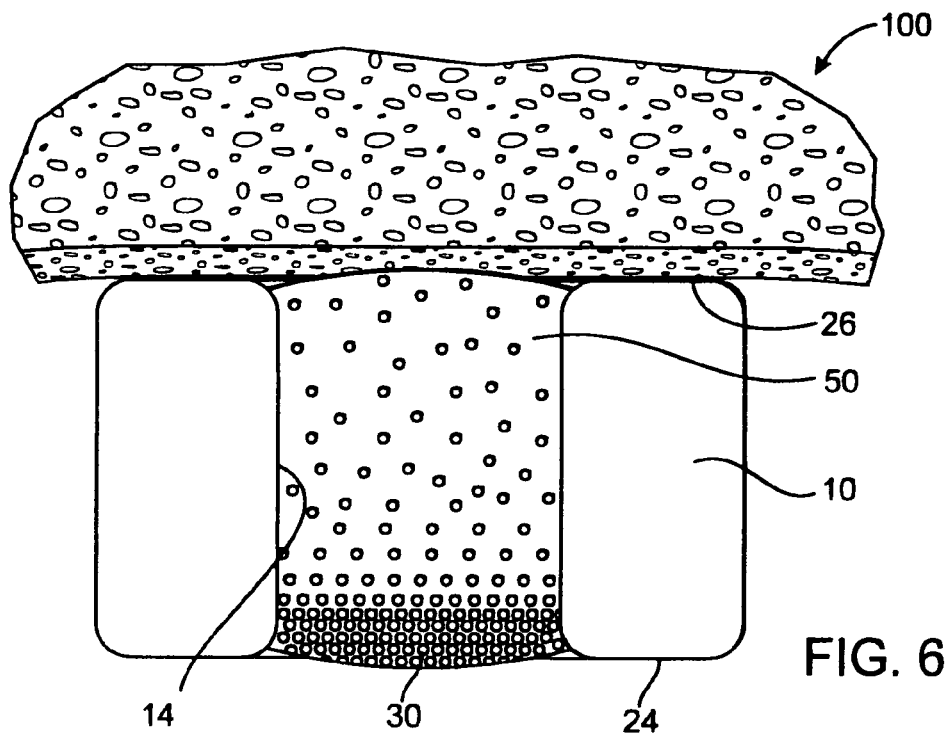
FIG. 6 is a side cross sectional view of another example of an opening in a stent matrix with one therapeutic agent having a concentration gradient.
Figure 7:
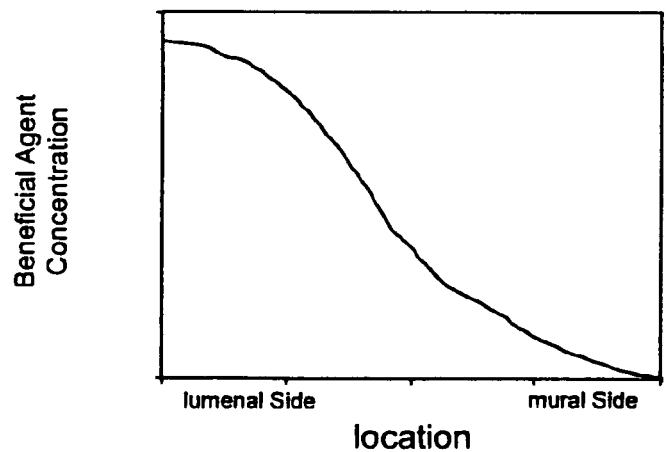
FIG. 7 is a graph of the therapeutic agent concentration gradient of FIG. 6.
Figure 8:
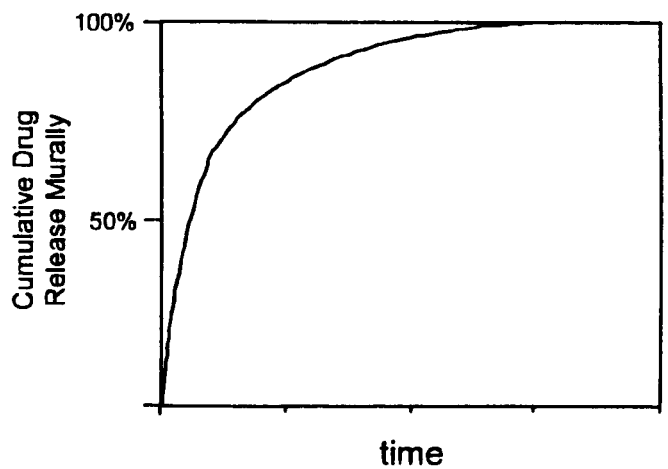
FIG. 8 is a graph of the release kinetics of the stent of FIG. 6.

FIG. 6 illustrates a configuration of a matrix 50 in an opening 14 where the matrix and therapeutic agent concentration gradient are designed for rapid initial release of agent to the luminal side followed by a low level release for an extended time. The agent concentration in FIG. 6 is high at the luminal surface 24 of the matrix 50 and the concentration gradient will decrease steeply in the interior of the matrix. FIG. 7 illustrates the concentration gradient of the FIG. 6 example graphically. FIG. 8 illustrates the agent release over time for the example of FIGS. 6 and 7. Using careful specification of the agent concentration gradient in this example, substantially first order agent release kinetics with directionally controlled delivery may be obtained.

Since the matrix is created in a stepwise manner, as will be described below, individual chemical compositions and pharmacokinetic properties can be imparted to different areas of the matrix. Numerous useful arrangements of such matrix areas can be formed, some of which will be described herein. Each of the areas of the matrix may include one or more agents in the same or different proportions from one area to the next. The matrix may be solid, porous, or filled with other drugs or excipients. The agents may be homogeneously disposed or heterogeneously disposed in different areas of the matrix.

Figure 9:
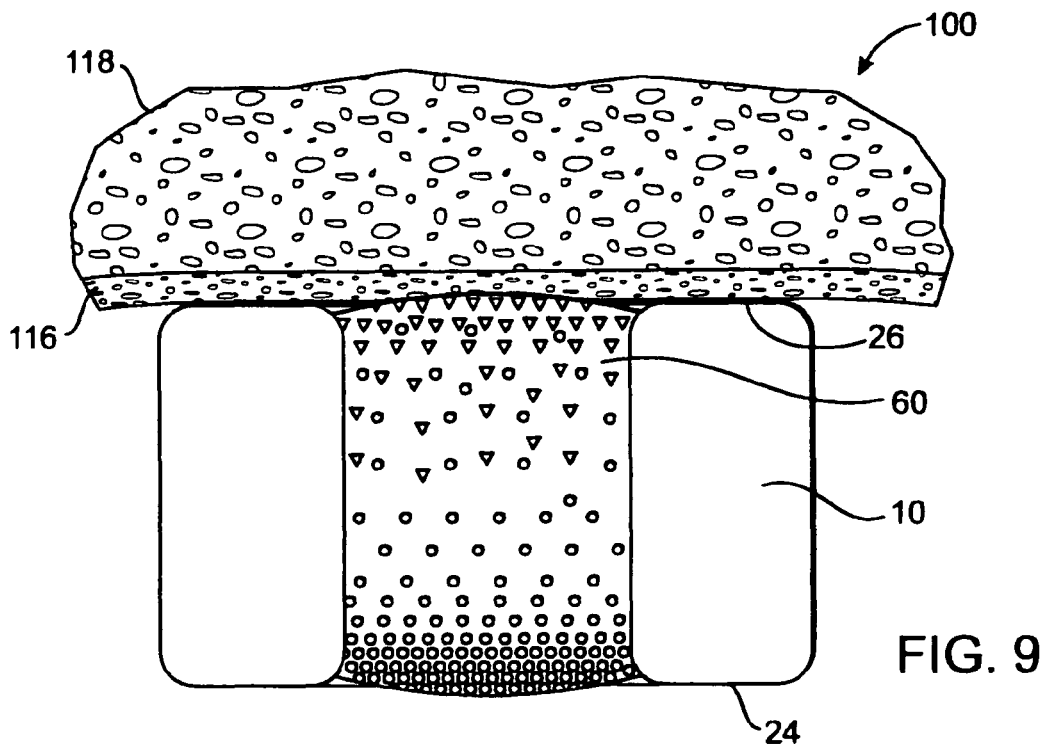
FIG. 9 is a side cross sectional view of an example of an opening in a stent showing a matrix with two therapeutic agents having concentration gradients.
Figure 10:
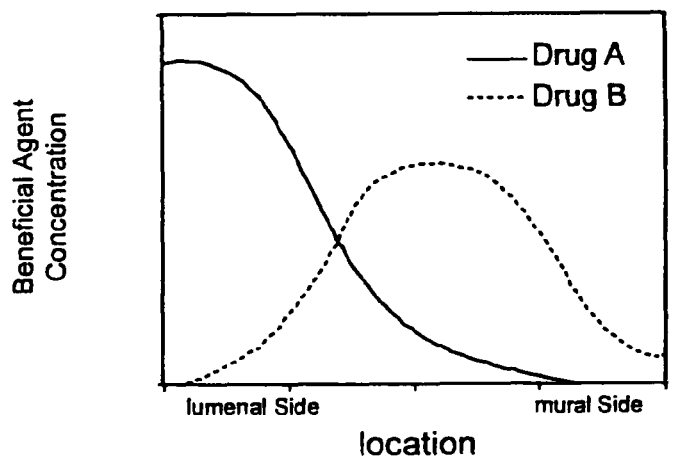
FIG. 10 is a graph of the therapeutic agent concentration gradients of FIG. 9.
Figure 11:
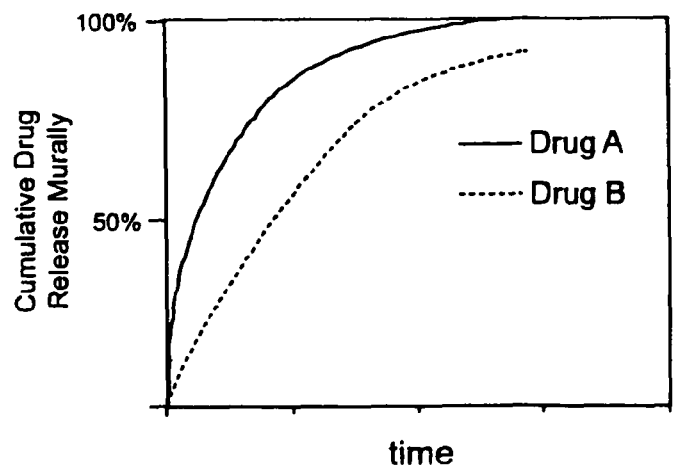
FIG. 11 is a graph of the release kinetics of the stent of FIG. 9.

FIG. 9 illustrates an example of another stent 10 having a matrix 60 containing two agents with different concentration gradients. In FIG. 9, a first agent (Drug A) represented by Os has a concentration gradient with a maximum concentration at a luminal side 24 of the stent. A second agent (Drug B) represented by ▼s has a concentration gradient with a maximum concentration at a mural side of the matrix. This configuration results in the delivery of two drugs in different primary delivery directions. For example, an antithrombotic agent (Drug A) may be delivered primarily luminally at a relatively quick initial release rate while an antirestenotic agent (Drug B) is delivered primarily murally with a different delivery profile having a more constant release rate and longer administration period. FIG. 10 illustrates graphically the agent concentration gradients of the first agent (Drug A) and the second agent (Drug B). FIG. 11 illustrates the cumulative release of the first and second agents (Drug A and Drug B) over time.

It is envisioned that the continuous agent concentration gradient will take a variety of forms depending on the desired administration period and rate of elution of the agent into the tissue surrounding the stent, as well as the desired direction of elution of agent from the stent, either mural or luminal. FIGS. 3-11 are merely illustrative of some of the concentration gradients which are useful. Further combinations of two or more agents with independent concentration gradients can provide a range of controlled release kinetic profiles of the agents from the matrix in or on the stent.

Therapeutic Agents

Some of the therapeutic agents for use with the present invention which may be transmitted primarily luminally, primarily morally, or both include, but are not limited to, antiproliferatives including paclitaxel and rapamycin, antithrombins, immunosuppressants including sirolimus, antilipid agents, anti-inflammatory agents, antineoplastics, antiplatelets, angiogenic agents, anti-angiogenic agents, vitamins, antimitotics, metalloproteinase inhibitors, NO donors, estradiols, anti-sclerosing agents and vasoactive agents, endothelial growth factors, estrogen, beta blockers, AZ blockers, hormones, statins, insulin growth factors, antioxidants, membrane stabilizing agents, calcium antagonists, retinoid, bivalirudin, phenoxodiol, etoposide, ticlopidine, dipyridamole, and trapidil alone or in combinations with any therapeutic agent mentioned herein. Therapeutic agents also include peptides, lipoproteins, polypeptides, polynucleotides encoding peptides, lipids, protein-drugs, protein conjugate drugs, enzymes, oligonucleotides and their derivatives, ribozymes, other genetic material, cells, antisense, oligonucleotides, monoclonal antibodies, platelets, prions, viruses, bacteria, and eukaryotic cells such as endothelial cells, stem cells, ACE inhibitors, monocyte/macrophages or vascular smooth muscle cells to name but a few examples. The therapeutic agent may also be a pro-drug, which metabolizes into the desired drug when administered to a host. In addition, therapeutic agents may be pre-formulated as microcapsules, microspheres, microbubbles, liposomes, niosomes, emulsions, dispersions or the like before they are incorporated into the therapeutic layer. Therapeutic agents may also be radioactive isotopes or agents activated by some other form of energy such as light or ultrasonic energy, or by other circulating molecules that can be systemically administered. Therapeutic agents may perform multiple functions including modulating angiogenesis, restenosis, cell proliferation, thrombosis, platelet aggregation, clotting, and vasodilation.

Anti-inflammatories include but are not limited to nonsteroidal inti-inflammatories (NSAID), such as aryl acetic acid derivatives, e.g., Diclofenac; aryl propionic acid derivatives, e.g., Naproxen; and salicylic acid derivatives, e.g., Diflusinal. Anti-inflammatories also include glucocoriticoids (steroids) such as dexamethasone, aspirin, prednisolone, triamcinolone, pirfenidone, meclofenamic acid, tranilast, and nonsteroidal anti-inflammatories. Anti-inflammatories may be used in combination with antiproliferatives to mitigate the reaction of the tissue to the antiproliferative.

The agents can also include anti-lymphocytes; anti-macrophage substances; cyclooxygenase inhibitors; immunomodulatory agents; anti-oxidants; cholesterol-lowering durgs; statins and angiotens in converting enzyme (ACE); fibrinolytics; inhibitors of the intrinsic coagulation cascade; antihyperlipoproteinemics; and anti-platelet agents; anti-metabolites, such as 2-chlorodeoxy adenosine (2-CdA or cladribine); immuno-suppressants including sirolimus, everolimus, tacrolimus, etoposide, and mitoxantrone; antileukocytes such as 2-CdA, IL-1 inhibitors, anti-CD116/CD18 monoclonal antibodies, monoclonal antibodies to VCAM or ICAM, zinc protoporphyrin; anti-macrophage substances such as drugs that elevate NO; cell sensitizers to insulin including glitazones; high density lipoproteins (HDL) and derivatives; and synthetic facsimile of HDL, such as lipator, lovestatin, pranastatin, atorvastatin, simvastatin, and statin derivatives; vasodilators, such as adenosine, and dipyridamole; nitric oxide donors; prostaglandins and their derivatives; anti-TNF compounds; hypertension drugs including Beta blockers, ACE inhibitors, and calcium channel blockers; vasoactive substances including vasoactive intestinal polypeptides (VIP); insulin; cell sensitizers to insulin including glitazones, P par agonists, and metformin; protein kinases; antisense oligonucleotides including resten-NG; antiplatelet agents including tirofiban, eptifibatide, and abciximab; cardio protectants including, VIP, pituitary adenylate cyclase-activating peptide (PACAP), apoA-I milano, amlodipine, nicorandil, cilostaxone, and thienopyridine; cyclooxygenase inhibitors including COX-1 and COX-2 inhibitors; and petidose inhibitors which increase glycolitic metabolism including omnipatrilat. Other drugs which may be used to treat inflammation include lipid lowering agents, estrogen and Adiponectin.

Agents may also be delivered using a gene therapy-based approach in combination with an expandable medical device. Gene therapy refers to the delivery of exogenous genes to a cell or tissue, thereby causing target cells to express the exogenous gene product. Genes are typically delivered by either mechanical or vector-mediated methods.

Some of the agents described herein may be combined with additives which preserve their activity. For example additives including surfactants, antacids, antioxidants, and detergents may be used to minimize denaturation and aggregation of a protein drug. Anionic, cationic, or nonionic detergents may be used. Examples of nonionic additives include but are not limited to sugars including sorbitol, sucrose, trehalose, dextrans including dextran, carboxymethyl (CM) dextran, diethylamino etyl (DEAE) detran; sugar derivatives including D-glucosaminic acid, and D-glucose diethyl mercaptal, synthetic polyethers including polyethylene glycol (PEG and PEO) and polyvinyl pyrrolidone (PVP); carboxylic acids including D-lactic acid, glycolic acid, and propionic acid; detergents with affinity for hydrophobic interfaces including n-dodecyl-β-D-maltoside, n-ocyl-β-D-glucoside, PEO-fatty acid esters (e.g. stearate (myrj 59) or oleate), PEO-sorbitan-fatty acid esters (e.g. Tween 80, PEO-20 sorbitan monooleate), sorbitan-fatty acid esters (e.g. SPAN 60, sorbitan monostearate), PEO-glyceryl-fatty acid esters; glyceryl fatty acid esters (e.g. glyceryl monostearate), PEO-hydrocarbon-esters (e.g., PEO-10 oleyl ether; triton X-100; and Lubrol. Examples of ionic detergents include but are not limited to fatty acid salts including calcium stearate, magnesium stearate, and zinc stearate; phospholipids including lecithin and phosphatidyl choline; CM-PEG; cholic acid; sodium dodecyl sulfate (SDS); docusate (AOT); and taumocholic acid.

Matrix Formation Methods

The agent matrix structure with the agent concentration gradient can be formed by several methods. According to one method, agent and polymer material are together converted into agent matrix reservoirs with an agent concentration gradient structure by first creating a homogeneous solution of agent and polymer carrier in a liquid form, such as in a solvent. One example of a solvent is one in which all agent and polymer are fully soluble at the respective concentrations desired for processing such that all ingredients are molecularly dissolved in the solvent.

Solvents may be water based, as when water soluble agents and water soluble polymers are the components of the agent delivery matrix. Alternatively, solvents can be mixtures of water with miscible organic solvents, such as dimethyl sulfoxide (DMSO), Nmethyl pyrrolidone (NMP), ethyl lactate (EL), dimethyl acetamide (DMAc), or simple alcohols. Additionally, non-aqueous solvents, predominantly organic solvents, can be suitable for non-water soluble polymers, such as poly(lactide-co-glycolide) polymers (PLGAs). Example organic solvents include DMSO, NMP, EL, anisole, chloroform, tetrahydrofuran (THF), xylene, and methylene chloride.

In the first method, steps (i) and (ii) are preformed followed by steps (iii) and (iv) which are repeated until the desired concentration gradient structure is obtained:

i) a solution comprised of suitable solvent and polymer material, and optionally a therapeutic agent, is introduced into an opening on the stent;

ii) the solvent is evaporated from the solution to form a first portion of matrix;

iii) a second solution is introduced which partially dissolves of otherwise liquifies the precedent material from step (ii) and allows partial mixing of the agent of precedent material and the components of the second solution to create a new hybrid solution in the cavity or hole in the stent; and iv) the solvent is evaporated from the newly formed hybrid solution to provide a portion of matrix having a concentration gradient of the agent therein. By changing the composition of successive solutions there will result a final agent containing matrix where the agent is present in a continuously changing concentration relative to the depth of the matrix, termed a concentration gradient.

Although the process has been described employing a solvent, a similar process may use a solution without a solvent when the polymer is heated to achieve a liquefied or flowable condition.

Two general sequences of solution compositions can provide the concentration gradient structure of the invention. In a first sequence, one or several iterations of the same agent and polymer compositions are introduced as described followed by successive iterations of solutions containing polymer only. In this manner a first portion of matrix is fabricated with an agent containing solution followed by introduction of a second portion of matrix without agent. The second portion of matrix without the agent introduced just after the first portion containing agent will extract a portion of agent from the first portion into itself, creating a concentration gradient of the agent in the combined structure after the solvent has evaporated. Successive additions of solutions with polymer and no agent will only be able to dissolve the portion formed just before, which has successively smaller amounts of agent, so as the depth of the matrix is increased by successive additions the agent proportion will be successively decreasing, continuing the formation of an agent concentration gradient.

Although the first method has been described with reference to depositing in a hole or cavity, the matrix may also be formed on the stent or in the stent in other configurations including coatings or partial coatings in substantially the same manner. Coatings are generally less preferable than reservoirs, as the depth of reservoirs permits more complex morphologies.

In a second sequence, a first series of iterations are done with a solution containing matrix and an agent at a first agent concentration, followed by a second series of iterations done with a solution having matrix and the agent at a second agent concentration. The resultant matrix will have a agent concentration gradient where the absolute concentration is near the first concentration at one side of the matrix, at an intermediate concentration in the middle of the matrix, and near the second agent concentration at the opposite side of the matrix.

In a second method an agent concentration gradient is formed in the matrix by a process of diffusion. A matrix containing no agent is first prepared from solutions containing polymer. The formed matrix is then immersed in a solution containing an agent for a time period to allow a partial diffusion of the agent from the solution into the matrix, then the matrix is removed from the solution. The resultant matrix will have a relatively higher agent concentration near the surface(s) that contacted the solution and lower concentration toward the opposite side, thus forming an agent concentration gradient across the depth of the agent containing matrix.

This second method can be performed with a matrix in the form of a coating on a stent or a partial coating on a stent, with a matrix within openings in a stent, a matrix prior to placing the matrix on or in the stent, or another matrix configuration. When the matrix is formed within openings in a stent a barrier layer may be placed on one side of the opening to allow diffusion of the agent into the matrix from primarily one side of the opening. The barrier layer may subsequently be removed if delivery from the barrier side is desired. Additional barrier layers may be added after formation of the concentration gradient if desired. The barrier layer can be a bioresorbable or non-bioresorbable.

EXAMPLE 1

Formulation Comprising a Gradient of a Therapeutic Agent

In the example below, the following abbreviations have the following meanings.

PLGA=poly(lactide-co-glycolide)
DMSO=Dimethyl sulfoxide
NMP=N-methylpyrrolidone
DMAC=Dimethyl acetamide A first mixture of high molecular weight PLGA and a suitable organic solvent, such as DMSO, NMP, or DMAC 93% wt. is prepared. The mixture is loaded dropwise into openings in the stent, then the solvent is evaporated to begin formation of the barrier layer. A one or more additional barrier layers are laid over the first by the same method of filling polymer solution into the hole followed by solvent evaporation.

A second mixture of paclitaxel and low molecular weight PLGA, in a suitable organic solvent, such as DMSO, is introduced into openings in the stent over the barrier layer. The solvent is evaporated to form a drug filled therapeutic agent layer. The filling and evaporation procedure is repeated until the hole is filled to about 50% of its total volume with drug in therapeutic agent layer layered on top of the barrier layer.

Multiple layers of a third solution, of low molecular weight PLGA and a suitable organic solvent, such as DMSO, are then laid down over the therapeutic agent layer to form the concentration gradient. When each of the third solution layers is loaded into the stent, a portion of the layer beneath is incorporated in the new layer. In this way the matrix is formed containing a concentration gradient of paclitaxel agent.

Following implantation of the filled stent in vivo, the paclitaxel contained within the stent is delivered slowly over a time period of about 5 to about 60 days, preferably about 10 to about 30 days. The barrier layer prevents the therapeutic agent from being delivered out the barrier layer side of openings in the stent. The barrier layer completely degrades after the administration of the paclitaxel.

While the invention has been described in detail with reference to the preferred embodiments thereof, it will be apparent to one skilled in the art that various changes and modifications can be made and equivalents employed, without departing from the present invention.

The invention claimed is:

1. An implantable medical device configured to release at least one therapeutic agent therefrom, the device comprising:
   an implantable body having a mural surface and a luminal surface; and
   a matrix affixed to the implantable body on said luminal surface, the matrix containing the at least one therapeutic agent therein, wherein the matrix is formed with an outer surface and an implantable body contacting surface such that the concentration of the therapeutic agent in the matrix varies as a gradient relative to the said surfaces of the matrix;
   wherein the concentration of the therapeutic agent in the matrix is higher at said luminal surface of the implantable body than at said mural surface of the implantable body;
   wherein the implantable body is substantially cylindrical and contains a plurality of struts therein, and the matrix is disposed in a plurality of holes passing through at least some of said struts in the implantable body, and the matrix is coated with a barrier layer at the luminal surface; and
   wherein the therapeutic agent has a maximum concentration substantially adjacent to the barrier layer and a minimum concentration substantially adjacent to said mural surface of the implantable body.

2. The device of claim 1, wherein the matrix comprises a bioresorbable polymer.

3. The device of claim 1, wherein the matrix is selected from the group consisting of poly(lactide-co-glycolide) (PLGA) and Poly vinylpyrrolidone (PVP).

4. The device of claim 1, wherein the at least one therapeutic agent comprises a plurality of therapeutic agents.

5. The device of claim 4, wherein the concentration of each of the therapeutic agents in the matrix vary with different continuous concentration gradients relative to the luminal surface of the implantable body.

6. The device of claim 1, wherein the therapeutic agent is selected from the group consisting of antithrombic agents, antiproliferative agents, and antirestenotic agents.

7. The device of claim 1, wherein the therapeutic agent elutes from the matrix at a rate that is controlled by the concentration gradient of the therapeutic agent in the matrix.

8. The device of claim 1, wherein the therapeutic agent is dissolved in the matrix in a solid solution morphology.

9. The device of claim 1, wherein the therapeutic agent is dispersed in the matrix in a solid emulsion morphology.

10. The device of claim 1, wherein the therapeutic also disposed as a coating on the luminal surface of the implantable body.

11. The device of claim 1, wherein the implantable medical device is a stent.

* * * * *